United States Patent
Moriya et al.

(10) Patent No.: US 8,183,031 B2
(45) Date of Patent: May 22, 2012

(54) COMPOSITION CONTAINING β-GLUCAN, METHOD OF PRODUCING THE SAME AND FOODS, DRINKS OR SKIN MOISTURIZERS CONTAINING THE COMPOSITION

(75) Inventors: Naoyuki Moriya, Minato-ku (JP); Yukiko Moriya, Minato-ku (JP); Koji Kubota, Minato-ku (JP)

(73) Assignee: Aureo Co., Ltd., Tokyo (JP)

( * ) Notice: Subject to any disclaimer, the term of this patent is extended or adjusted under 35 U.S.C. 154(b) by 1389 days.

(21) Appl. No.: 11/575,047

(22) PCT Filed: Aug. 3, 2005

(86) PCT No.: PCT/JP2005/014233
§ 371 (c)(1),
(2), (4) Date: Mar. 9, 2007

(87) PCT Pub. No.: WO2006/027914
PCT Pub. Date: Mar. 16, 2006

(65) Prior Publication Data
US 2008/0293669 A1  Nov. 27, 2008

(30) Foreign Application Priority Data
Sep. 9, 2004 (JP) ................................ 2004-262450

(51) Int. Cl.
*A01N 63/00* (2006.01)
*A01N 63/04* (2006.01)
*C12N 1/00* (2006.01)

(52) U.S. Cl. ............... 435/255.1; 424/93.51; 435/255.7; 435/911

(58) Field of Classification Search .................. None
See application file for complete search history.

(56) References Cited

U.S. PATENT DOCUMENTS

| 7,442,541 | B2 * | 10/2008 | Tsubaki et al. | ............ 435/254.1 |
|---|---|---|---|---|
| 2005/0272694 | A1 | 12/2005 | Moriya et al. | |

FOREIGN PATENT DOCUMENTS

| JP | 61 146192 | 7/1986 |
|---|---|---|
| JP | 62 205008 | 9/1987 |
| JP | 7 51080 | 2/1995 |
| JP | 7-51080 | 2/1995 |
| JP | 7-51082 | 2/1995 |
| JP | 9 56391 | 3/1997 |
| JP | 9-56391 | 3/1997 |
| JP | 10 276740 | 10/1998 |
| JP | 2002 204687 | 7/2002 |
| JP | 2002-204687 | 7/2002 |
| KR | 2003-0039872 | 5/2003 |

OTHER PUBLICATIONS

Nobutake Hamada, et al., "Ascorbic Acid Stimulation of Production of a Highly Branched β-1,3-Glucan by Aureobasidium pullulans K-1—Oxalic Acid, a Metabolite of Ascorbic Acid as the Stimulating Substance", Biosci. Biotechnol. Biochem., vol. 64, No. 9, XP-009049436, Jan. 1, 2000, pp. 1801-1806.

* cited by examiner

*Primary Examiner* — Debbie K Ware
(74) *Attorney, Agent, or Firm* — Oblon, Spivak, McClelland, Maier & Neustadt, L.L.P.

(57) ABSTRACT

It is intended to utilize β-glucan produced by a bacterium belonging to *Aureobasidium* sp. From a bacterium belonging to *Aureobasidium* sp., a mutant with little pigment accumulation is constructed by a mutagenesis means of, for example, irradiating with ultraviolet light or treating with a mutagen. A culture obtained by culturing this mutant in a liquid culture medium is usable as a composition with a large β-glucan content without showing any intense dark green color caused by the accumulation of melanin-like pigments. This composition may be taken as such as a functional food having the physiologically active functions of the β-glucan-containing composition. Alternatively, it may be added to foods, drinks, food additives, cosmetics and so on.

7 Claims, 5 Drawing Sheets

[Figure 1]
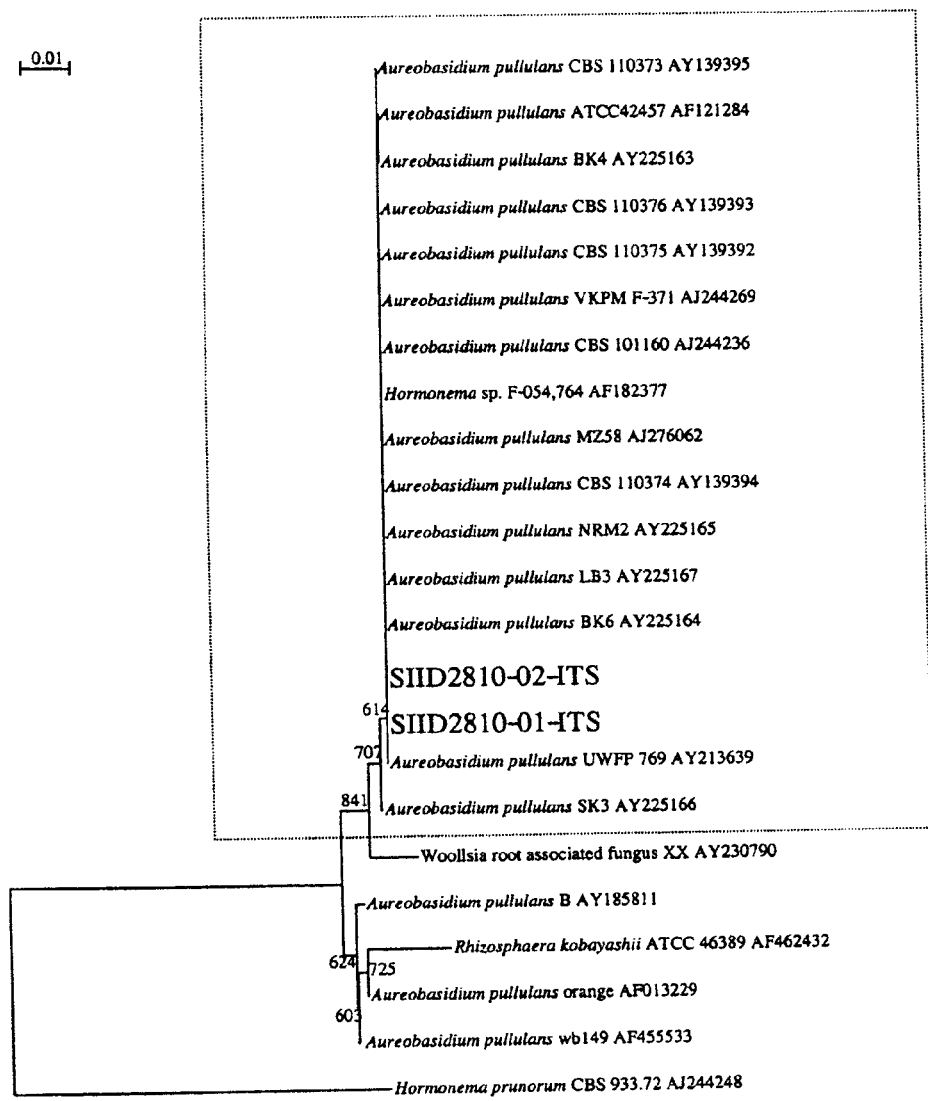

[Figure 2]
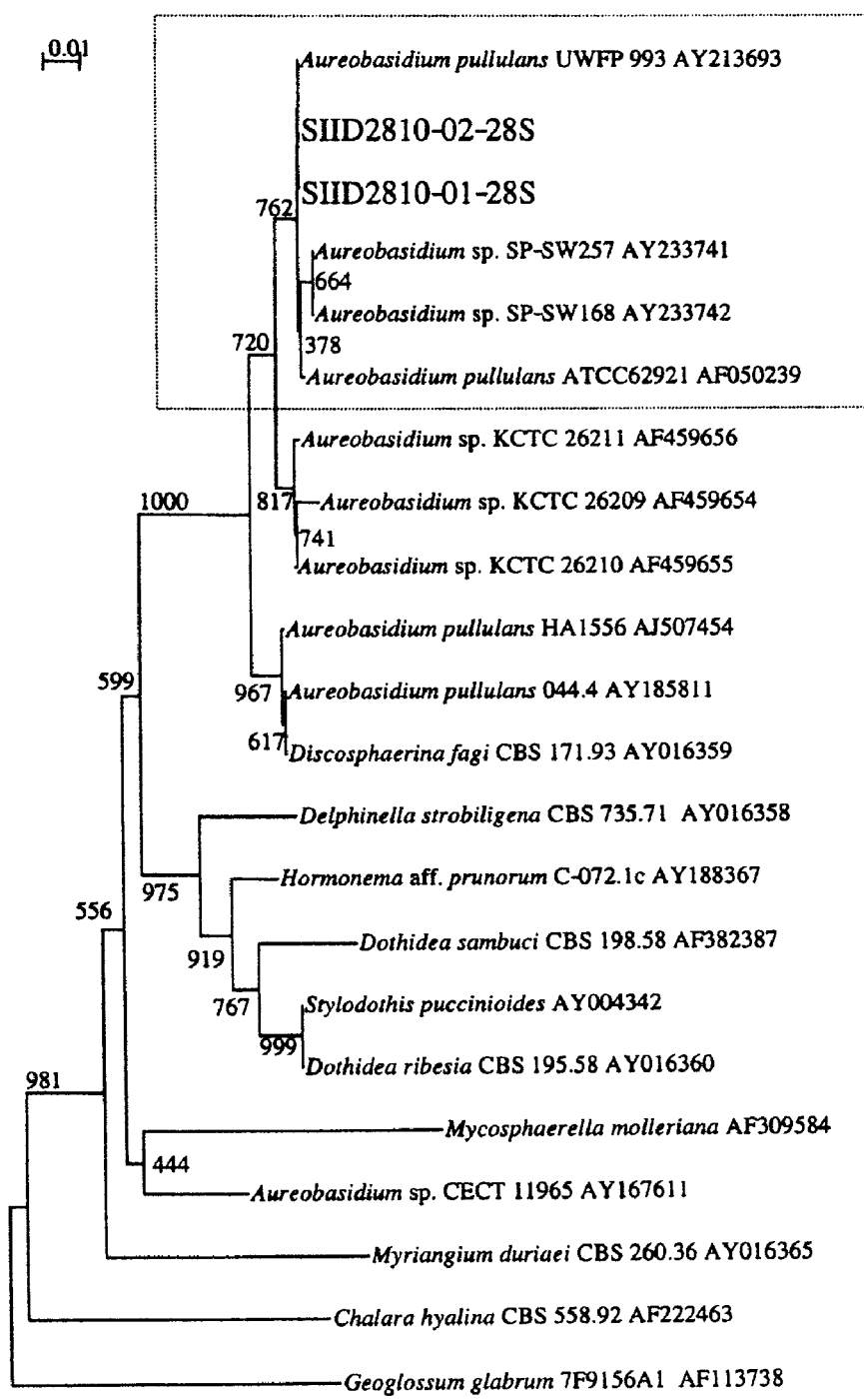

[Figure 3]
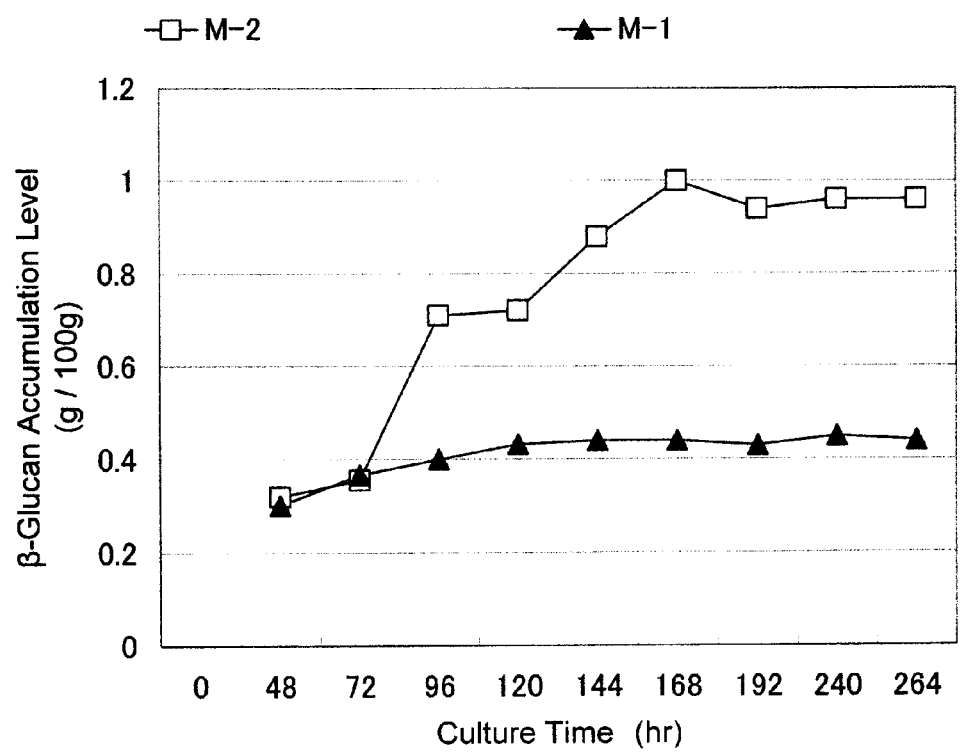

[Figure 4]
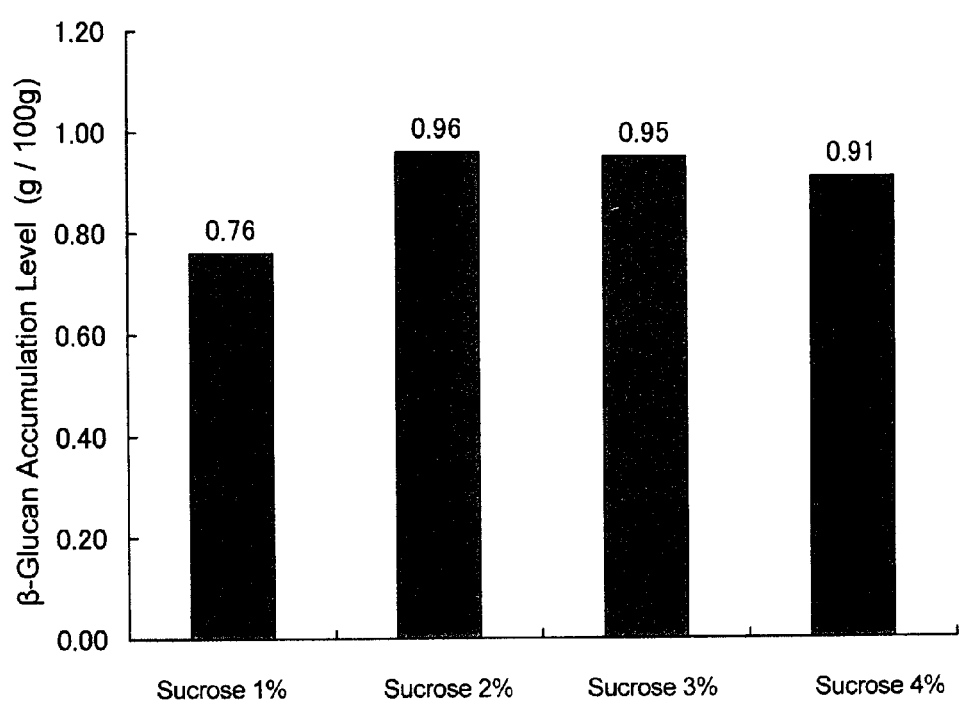

[Figure 5]
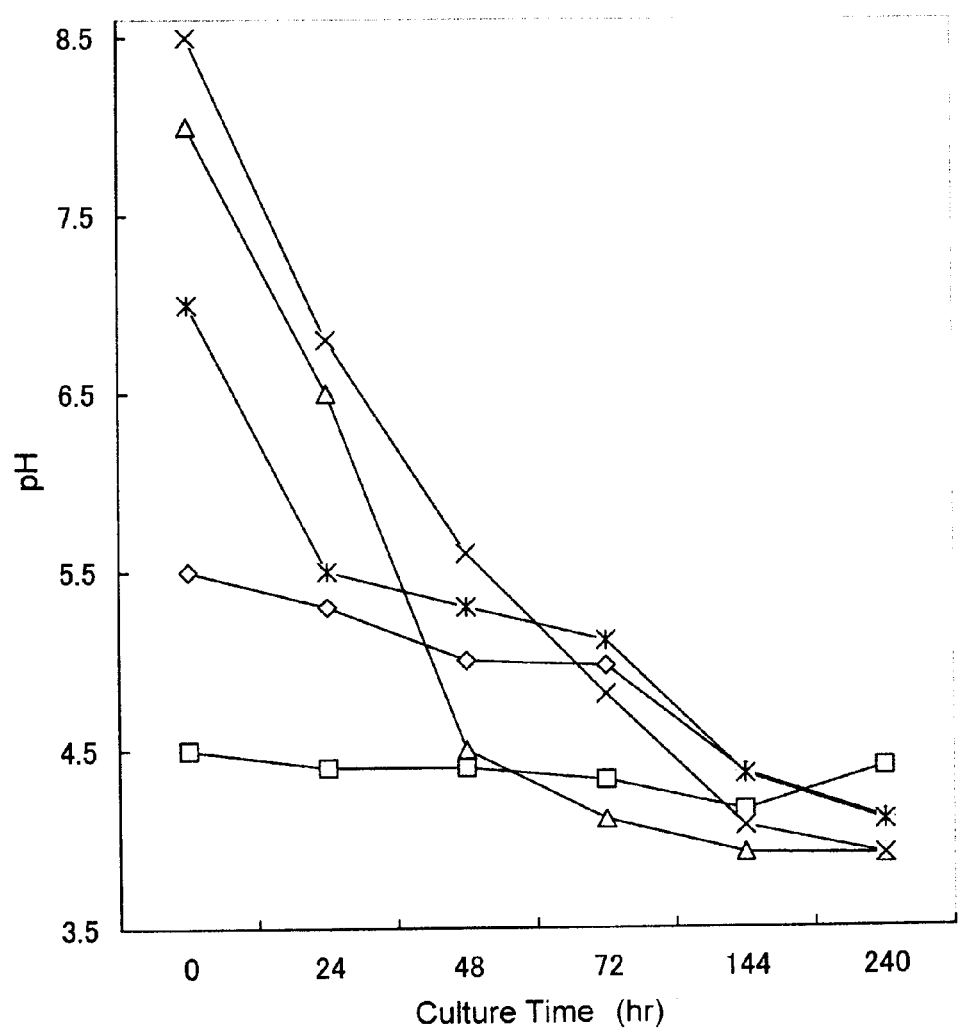

COMPOSITION CONTAINING β-GLUCAN, METHOD OF PRODUCING THE SAME AND FOODS, DRINKS OR SKIN MOISTURIZERS CONTAINING THE COMPOSITION

This application is a filing under 35 U.S.C. §371, of International Application No. PCT/JP05/14233, filed on Aug. 3, 2005; and which claims priority to Japanese Application No. 2004-262450, filed on Sept. 9, 2004.

TECHNICAL FIELD

The present invention relates to a β-glucan-containing composition, which contains a cultured product of a microorganism belonging to the genus *Aureobasidium* sp., and to a method of producing the composition. The present invention further relates to food and drink or a skin moisturizer using the composition.

BACKGROUND ART

β-glucan is a polysaccharide which is composed of D-glucose as a constituent saccharide. For example, β-1,3-glucan is a polysaccharide composed of polymerized cyclic β-pyranose D-glucose molecules in which cyclic β-pyranose D-glucose molecules are bound to each other to condense via β-1,3-glucoside bonds between a hydroxyl moiety binding to a carbon atom at position 1 in a glucose molecule and a hydroxyl moiety binding to a carbon atom at position 3 in another glucose molecule. Various types of the polysaccharides such as β-glucan can be found in organisms in nature as storage molecules of saccharide that is an energy source and as structural molecules of cell walls or the like. The β-glucan contained in mushroom such as *agaricus* mushroom (*Agaricus brazei*) reishi mushroom (*Ganoderma lucidum*), *Grifola frondosa*, and *Lentinula edodes* is known to have various physiological activities for maintaining or promoting health. There have been made a number of attempts to utilize the β-glucan as a functional material, a pharmaceutical product, and the like which are intended for an immunopotentiating action, an anti-tumor activity, a cancer cell proliferation suppressing action, an antiallergic action, an antiinflammatory action, a cholesterol reducing action, an antithrombotic action, an action of dietary fiber, an antihypertensive action, an antidiabetic action, an improvement of hepatic function, or the like. In addition, the β-glucan is attracting expectations to be a polysaccharide functional material which can be expected to be applied to a wide spectrum of applications such as antiflatulents for preventing or relieving constipation since the β-glucan is indigestible, and cosmetics which utilize moisture retention properties of the β-glucan.

As β-glucan having beneficial activities, there is well known β-1,3-1,6-glucan having a main chain composed of β-1,3-glucoside bonds and a side chain of D-glucose from a carbon atom at position 6. The branching structure is thought to be necessary for the activities, but the mechanism of the action has not been fully clarified. In addition, β-glucan is a high-molecular weight polymer obtained from a natural substance. Therefore, the structure of β-glucan, such as a degree of branching the length of the main chain, the length of the side chain, or the like, and the presence or absence of and the degree of modification of a D-glucose hydroxyl group by amination, phosphorylation, methylation, acetylation, or the like are not uniform. The principle regarding the effects of the structure and chemical modification on the activities have not been presented. Thus, the β-glucan derived from mushroom has been preferably used only empirically in part, and there have been few attempts to utilize β-glucan derived from other organism species.

Recently, it has been found that β-1,3-1,6-glucan which is produced by a microorganism belonging to the genus *Aureobasidium* sp. (commonly known as "black yeast"), which is an imperfect fungi widely exist in the nature exhibits a function equivalent or superior to that of the β-glucan derived from mushroom.

For example, Patent Document 1 describes that an extracellular homopolysaccharide produced by a microorganism belonging to the genus *Aureobasidium* sp. is β-1,3-1,6-glucan.

In addition, Patent Document 2 describes that an *Aureobasidium* culture solution containing as a main component β-1,3-1,6-glucan has high antitumor activity and high immunopotentiating activity via oral administration, so the solution can be applied as a pharmaceutical product for various diseases.

Patent Document 1: JP-A-10-276740
Patent Document 2: JP-A-2002-204687

DISCLOSURE OF THE INVENTION

Problems to be Solved by the Invention

Culture of typical mushroom requires cultivation of the mushroom. However, the microorganism belonging to the genus *Aureobasidium* sp., that is an imperfect fungi, can be cultured with aeration in a liquid nutrient medium, so the microorganism can efficiently be mass-produced. In addition, the microorganism releases β-glucan outside of a microbial cell thereof and a high concentration of the β-glucan is accumulated in the culture solution of the microorganism, so the culture solution can be utilized as a composition containing a high concentration of β-glucan without extraction from the microbial cells. In addition, the cultured product containing the microbial cells can be utilized as a functional material with which composite effects are expected, which concomitantly contains other active ingredients contained in the microbial cells.

However, a culture solution of the microorganism belonging to the genus *Aureobasidium* sp. which is typically called "black yeast" shows a dark green color caused by accumulation of melanin-like substances, so there has been a problem in that the cultured product or culture solution of the microorganism has a deteriorated looking and thus is avoided when they are used without any modification for foods and drinks, cosmetics, and the like. In addition, the melanin pigment can be removed through a purification process, but the purification generally accompanies a complex process, so it is difficult to directly extract β-glucan derived from a natural substance.

Thus, it is an object of the present invention to provide a β-glucan-containing composition derived from natural yeast, which has a low pigment accumulation property and a high β-glucan productivity, and a method of producing the composition.

Means for Solving the Problems

In order to achieve the above-mentioned object, the inventors of the present invention have made extensive investigation. As a result, the inventors of the present invention have created a mutant strain having properties including a lowered accumulation of pigment from a microorganism belonging to the genus *Aureobasidium* sp., and thus have completed the present invention.

That is, a β-glucan-containing composition of the present invention includes: a cultured product obtained by culturing a mutant strain in a liquid medium, the mutant strain created by subjecting a microorganism belonging to the genus *Aureobasidium* sp. as a parent strain to an irradiation with ultraviolet light or a treatment with a mutagen to mutagenize, and the mutant strain having properties including a lowered accumulation of pigment than that of the parent strain; in which the β-glucan-containing composition has a β-glucan content of 0.3% by mass or more.

According to the β-glucan-containing composition of the present invention, there can be provided a β-glucan-containing composition which contains a high concentration of β-glucan, the β-glucan produced by a microorganism belonging to the genus *Aureobasidium* sp. outside of microbial cells thereof during proliferation, as well as which has a low degree of pigmentation.

In the β-glucan-containing composition of the present invention, it is preferable that the degree of pigmentation of the cultured product be represented by a lightness L* value be 10 or more. According to the present aspect of the invention, there can be provided a β-glucan-containing composition which contains a high concentration of the β-glucan and at the same time which does not affect merchantability of a product owing to the impression from the exterior.

In addition, in the β-glucan-containing composition of the present invention, it is preferable that the parent strain be a microorganism belonging to *Aureobasidium pullulans*. According to the present aspect of the invention, microorganisms whose microbiological properties are well known can be used as raw materials.

Further, in the β-glucan-containing composition of the present invention, it is preferable that the mutant strain be *Aureobasidium pullulans* M-2 (FERM BP-10014). According to the present aspect of the invention, microorganisms whose microbiological properties are well known and which are easily available and highly safe can be used as raw materials.

A method of producing a β-glucan-containing composition of the present invention includes culturing a mutant strain in a liquid medium, the mutant strain created by subjecting a microorganism belonging to the genus *Aureobasidium* sp. as a parent strain to an irradiation with ultraviolet light or a treatment with a mutagen to mutagenize, and the mutant strain having properties including a lowered accumulation of pigment than that of the parent strain, whereby the culture produces 0.3% by mass or more of β-glucan contained in the cultured product thereof.

According to the method of producing a β-glucan-containing composition of the present invention, a β-glucan-containing composition, which contains a high concentration of β-glucan, the β-glucan produced by a microorganism belonging to the genus *Aureobasidium* sp. outside of microbial cells thereof during proliferation, as well as which has a low degree of pigmentation, can efficiently be produced by culturing the aforementioned mutant strain in a liquid medium.

In the method of producing a β-glucan-containing composition of the present invention, it is preferable that the cultured product have a degree of pigmentation represented by a lightness L* value of 10 or more. According to the present aspect of the invention, there can be efficiently produced a β-glucan-containing composition which contains a high concentration of the β-glucan and at the same time which does not affect merchantability of a product owing to the impression from the exterior.

In addition, in the method of producing a β-glucan-containing composition of the present invention, it is preferable that the parent strain be a microorganism belonging to *Aureobasidium pullulans*. According to the present aspect of the invention, microorganisms whose microbiological properties are well known can be used as raw materials.

Further, in the method of producing a β-glucan-containing composition of the present invention, it is preferable that the mutant strain be *Aureobasidium pullulans* M-2 (FERM BP-10014). According to the present aspect of the invention, microorganisms whose microbiological properties are well known and which are easily available and highly safe can be used as raw materials.

In a preferable aspect of the method of producing a β-glucan-containing composition of the present invention, it is preferable that the culture be performed in a state where the liquid medium has a pH value of 4.5 to 6.0.

According to the preferable aspect of the invention, the culture solution has a pH value in a range from 4.5 to 6.0 during culture for producing β-glucan. In particular, the pH value becomes less than 5.0 in last half of the culture. Therefore, quality deterioration due to saprophytic contamination is difficult to occur, and heat sterilization required after completion of the culture becomes easy.

Further, another aspect of the method of producing a β-glucan-containing composition of the present invention may include the further steps of: adjusting the pH value of the resultant cultured product to less than 4.5 by addition of vitamin C and/or an organic acid; and subjecting the resultant cultured product to heat sterilization.

According to the another aspect of the invention, it is easy to sterilize under a mild heat condition which is adopted for a composition having a pH value of less than 4.5 and which is defined by the manufacture standard of the food hygiene law. Thus, there can be provided a β-glucan-containing composition, which has properties of the above-mentioned β-glucan-containing composition of the present invention and in which a change in properties as a food additive, such as texture, coloration, taste, and flavor, caused by heat is minimized. In addition, the composition can be made into a composition which contains vitamin C and/or an organic acid having various physiologically active functions such as an antioxidative properties and at the same time which has a refreshing taste.

Meanwhile, the food and drink of the present invention contains the β-glucan-containing composition which is obtained by the above-mentioned aspect of the present invention. According to the food and drink of the present invention, there can be provided food and drink for easily and safely ingesting β-glucan that is a polysaccharide derived from the *Aureobasidium* and at the same time which has a low degree of pigmentation.

Further, the skin moisturizer of the present invention contains the β-glucan-containing composition, which is obtained by the above-mentioned aspect of the present invention. According to the present aspect of the invention, there can be provided a skin moisturizer utilizing moisture retention properties of β-glucan that is a polysaccharide derived from the *Aureobasidium* without affecting the merchantability of a product owing to the impression from the exterior.

A mutant strain of a microorganism belonging to the genus *Aureobasidium* sp. of the present invention is characterized by being created by subjecting a microorganism belonging to the genus *Aureobasidium* sp. as a parent strain to an irradiation with ultraviolet light or a treatment with a mutagen to mutagenize, and having properties including a lowered accumulation of pigment than that of the parent strain and an increased accumulation of β-glucan than that of the parent strain.

According to the mutant strain of a microorganism belonging to the genus Aureobasidium sp. of the present invention, there can be provided a β-glucan-containing composition, which contains a high concentration of β-glucan, the β-glucan produced by a microorganism belonging to the genus Aureobasidium sp. outside of microbial cells thereof during proliferation, as well as which has a low degree of pigmentation. Further, there can be provided food and drink, a skin moisturizer, or the like which contains β-glucan and which does not affect the merchantability of a product owing to the impression from the exterior.

In addition, in a preferable aspect of the mutant strain of a microorganism belonging to the genus Aureobasidium sp. of the present invention, it is preferable that the mutant strain be Aureobasidium pullulans M-2 (FERM BP-10014). According to the present aspect of the invention, a mutant strain, which maintains microbiological properties equivalent to those of a parent strain thereof except for the pigment accumulation and the β-glucan accumulation, can be used as a raw material for the composition, food and drink, skin moisturizer, and the like each containing β-glucan.

EFFECTS OF THE INVENTION

According to the present invention, there can be simply obtained a β-glucan-containing composition, which has a low degree of pigmentation and contains a high concentration of β-glucan.

In addition, in the method of producing a β-glucan-containing composition of the present invention, when the culture is performed in a state where the pH value of the liquid medium is 4.5 to 6.0, especially when the pH value is low in a later stage of the culture, quality deterioration due to saprophytic contamination by saprophytes is difficult to occur during the production step, so the heat sterilization treatment required from a perspective of food hygiene can be performed under a milder condition.

BRIEF DESCRIPTION OF THE DRAWINGS

FIG. 1 shows a molecular phylogenetic tree created by the neighbor-joining method on the basis of a base sequence of a ribosomal RNA gene region (1): ITS-5.8S region.

FIG. 2 shows a molecular phylogenetic tree created by the neighbor-joining method on the basis of a base sequence of a ribosomal RNA gene region (2): 28SrRNA-D1/D2 region.

FIG. 3 shows changes with time of accumulation amounts of a polysaccharide mainly composed of β-glucan, which is released into and accumulates in a culture solution.

FIG. 4 shows effects of a sucrose concentration in a nutrient medium on a production amount of the polysaccharide mainly composed of β-glucan, which is released into and accumulates in a culture solution.

FIG. 5 shows changes with time in pH in a culture period of culture solutions having different initial pH at the time of inoculation.

BEST MODE FOR CARRYING OUT THE INVENTION

The microorganism to be used as a parent strain in the present invention may be a microorganism which belongs to the genus Aureobasidium sp. and which can produce β-glucan. An example of the microorganism which can be used is Aureobasidium pullulans M-1 (Accession No. FERM BP-08615 deposited in International Patent Organism Depositary, National Institute of Advanced Industrial Science and Technology).

Means for mutagenesis in the present invention may be an irradiation with ultraviolet light or a treatment with a mutagen, which is generally used for obtaining a mutant strain of a microorganism. Examples of the mutagen, which can be used, include typical mutagens such as ethyl methane sulfonate, nitrosoguanidine, and ethidium bromide. In addition, a UV lamp or the like can be used for the irradiation with ultraviolet light.

The mutant strain of the present invention which has properties including a lowered accumulation of pigment than that of a parent strain thereof can be created with good reproducibility by: culturing on an agar-plate medium a microbial cell population of a microorganism belonging to the genus Aureobasidium sp. which has been treated by a means for mutagenesis; and isolating the colony which does not exhibit green color. It is preferable that the mutant strain maintain the same microbiological properties as those of the parent strain except for the pigment accumulation and the β-glucan accumulation. An example of the mutant strain which can be used is Aureobasidium pullulans M-2 (Accession No. FERM BP-10014 deposited in International Patent Organism Depositary, National Institute of Advanced Industrial Science and Technology) which is derived from a parent strain thereof. Aureobasidium pullulans M-1.

In the present invention, the microorganism to be used as the parent strain and the mutant strain thereof (hereinafter, they are referred to as "Aureobasidium") can be cultured on a general nutrient medium. An example of the nutrient medium which can be used is, but not particularly limited to, a liquid medium (pH 5.2 to 5.4) containing 1% of sucrose, 0.2% of ascorbic acid, and 0.2% of rice polishings. The Aureobasidium can stably proliferate and be maintained by culturing it at a temperature of 20 to 30° C. with aeration, and preferably with aeration and stirring. In addition, the Aureobasidium can be cultured on an agar-plate medium to form a colony.

According to the preferable aspect of the liquid culture, when the Aureobasidium proliferates in a predetermined amount of a liquid medium, a culture solution thereof generally contains 0.6 to 1.8% by mass of solid matter which contains 5 to 90% by mass of β-glucan at a stage where the Aureobasidium has consumed nutrient components for the proliferation thereof in the liquid culture and has reached the proliferation stationary phase. In this case, the culture solution means the portion of solution which is obtained by removing the portion of proliferated microbial cell from a cultured product after the culture by centrifugation or filtration, and the solid matter contained in a culture solution means components other than water of the solution. In addition, components containing β-glucan may be contained in a released component which has been released outside of microbial cells but has not been dispersed in a solution. Note that, as described above, the main high-molecular weight polysaccharide produced by the Aureobasidium is β-1,3-1,6-glucan having a structure in which a main chain formed by glucose via β-1,3 bonds has branches formed by glucose via β-1,6 bonds. The β-glucan which is produced and released by the Aureobasidium in the present invention does not significantly differ from the β-1,3-1,6-glucan in terms of the constitution and degree of branching of the structure.

The mutant strain to be created in the present invention is preferably a mutant strain having β-glucan accumulation properties in which β-glucan is released in a solution obtained when as described above the mutant strain is allowed to proliferate in a predetermined amount of a liquid medium and removing the portion of microbial cell from a thus-obtained cultured product by centrifugation, filtration, or the like in an amount 1.5 folds or more, or more preferably 3 folds or more than that released from the parent strain thereof. By using the mutant strain, there can easily be obtained a β-glucan-containing composition of the present invention, which contains 0.3% by mass or more of the β-glucan with respect to a total weight of a cultured product after culture.

In the present invention, the pigment accumulation properties of the *Aureobasidium* and the degree of pigmentation of a culture solution can each be determined by qualitative analysis of color components thereof using a spectral calorimeter, a colorimeter/differential calorimeter, or the like. For example, the analysis can be performed using a commercially available "spectral colorimeter JS555" (trade name, manufactured by Color Techno System Corporation). In this case, a lightness L* value which is represented as a numeral value a degree of lightness by a lightness element (L) that indicates a region from black to white can be used as an index in Lab color coordinate system which is standardized by CIE (International Commission on Illumination), that is, one of color models which quantifies color information.

In general, the *Aureobasidium* has properties for producing melanin-like substances. A cultured product thereof, in which the melanin-like substances are accumulated when the culture reaches the proliferation stationary phase according to the aforementioned preferable aspect of the liquid medium, shows a dark green color and has a lightness L* value of less than 10.

The mutant strain to be created in the present invention has pigment accumulation properties where the difference in the lightness L* value is preferably 5 or more, more preferably 10 or more, and further preferably 20 or more in a comparison of the degree of pigmentation of cultured products to the parent strain. By using such mutant strain, the degree of pigmentation of the cultured product obtained by accumulation of the melanin-like substances in the proliferation stationary phase can be set to 10 or more in the lightness L* value.

The β-glucan-containing composition of the present invention may be a cultured product itself which is obtained by allowing the mutant strain to proliferate in a predetermined amount of a liquid medium as described above. Alternatively, the β-glucan-containing composition of the present invention may be a part of the cultured product, that is, the portion of solution which is obtained by separating and removing the portion of microbial cell moiety from the cultured product by centrifugation, filtration, or the like. In other words, in a case where the β-glucan-containing composition is a cultured product itself, the composition contains microbial cells of the *Aureobasidium* and concomitantly contains β-glucan which has been released inside and outside of the microbial cells but has not been dispersed in the solution, staying on surfaces of the microbial cells. In addition, in a case where the β-glucan-containing composition is the properties of solution of the cultured product, the composition does not contain the microbial cells of the *Aureobasidium*. Thus, respective types of the compositions can be used depending on each application.

From the β-glucan-containing composition of the present invention, low-molecular weight substances can be removed in such a manner that the portion of solution of the cultured product is additionally subjected to an ethanol precipitation treatment or the like to separate and concentrate β-glucan in the precipitates, to thereby remove the low-molecular weight substances which are not separated and concentrated in the precipitates by the ethanol treatment or the like.

In the β-glucan-containing composition of the present invention, a blend ratio of β-glucan produced by the *Aureobasidium*, which is contained in solid matter other than water in the β-glucan-containing composition is preferably 5 to 90% by mass, and more preferably 20 to 90% by mass in terms of β-glucan.

The β-glucan-containing composition of the present invention can be used without a sterilization treatment. However, in general, it is preferable that the cultured product be sterilized, or the portion of solution obtained by separating and removing the portion of microbial cell from the cultured product by centrifugation, filtration, or the like be sterilized by heat or by heat with pressure. In those cases, the pH value of the composition can be adjusted to less than 4.5, or more preferably less than 4.0 with a pH adjuster such as vitamin C or an organic acid, and the sterilization can be performed under a mild heat condition defined by the manufacture standard of the food hygiene law, to thereby minimize the change in properties as food such as texture, coloration, taste, and flavor. Further, the addition of vitamin C and/or an organic acid can impart various physiological functions such as antioxidative properties, and also can impart a refreshing taste to the β-glucan-containing composition of the present invention.

The β-glucan-containing composition of the present invention can appropriately be blended with vitamins, minerals, oligosaccharides, dietary fiber, polyphenols, and the like in addition to the polysaccharide produced by the *Aureobasidium* such as the β-1,3-1,6-glucan and the other components.

The β-glucan-containing composition of the present invention can be prepared into various preparations by a generally-used preparation method. From the perspective of solubility, it is preferable to prepare powder or granules of the composition using powdery or granules-producing process such as freeze-drying, spray granulation, and the like. In addition, a capsule, a tablet, or the like can be prepared from the powder or granules.

The β-glucan-containing composition of the present invention can be formulated in various foods and drinks such as a refreshing drink, milk, yogurt, a lactic acid drink, a jelly drink, a fruit juice drink, vegetable juice, soup, miso soup, and the like.

In a case where the β-glucan-containing composition of the present invention is orally ingested, the ingestion amount thereof per day is not particularly limited, but it is preferable to ingest 0.5 mg to 10 mg/Kg/day in terms of β-glucan.

For the skin moisturizer containing the β-glucan-containing composition of the present invention, the β-glucan-containing composition may directly be used as toner or a cosmetic liquid, or may be appropriately blended with various cosmetics for skin such as an emulsion, cream, and pack. The β-glucan-containing composition is contained in the skin moisturizer in a blend ratio of preferably 0.5 to 50% by mass, and more preferably 5 to 20% by mass.

EXAMPLES

Hereinafter, the present invention will be described in detail by way of examples. However, the scope of the present invention is not limited by these examples.

Example 1

Creation of *Aureobasidium pullulans* M-2

A parent strain, that is, *Aureobasidium pullulans* M-1 (Accession No. FERM BP-08615 deposited in International Patent Organism Depositary, National Institute of Advanced Industrial Science and Technology) was cultured on a PDA (Potato Dextrose Agar, manufactured by Difco Laboratories Inc.) slant for 7 days. The resultant microbial cells were suspended in 10 ml of PBS to make a solution containing the microorganism in a concentration of about 1,000 CFU/ml. 0.2 ml of the microbial cell suspension was applied onto a PDA (Potato Dextrose Agar, manufactured by Difco Laboratories Inc.) plate. After that, the microbial cells on the plate were treated with UV light irradiation for different time periods, that is, 0, 5, and 10 minutes. The plates were subjected to static culture at 25° C. for 4 days to confirm colony formation. Further, the plates were subjected to culture at 4° C. for 3 days to make the microbial cells be chlamydospores. White colonies were selected from those plates to isolate a plurality of mutant strains. The emergence frequency of the white colony was about 1/1,200.

One of the obtained mutant strains was named *Aureobasidium pullulans* M-2, and was deposited in International Patent Organism Depositary, National Institute of Advanced Industrial Science and Technology with Accession No. FERM BP-10014.

To compare microbiological properties of *Aureobasidium pullulans* M-2 with those of the parent strain *Aureobasidium pullulans* M-1, colonies cultured on an agar-plate medium for 1 week was subjected to macroscopic observation for the diameter, color tone, surface characteristics, presence or absence of soluble pigment production, and the like. In addition, microscopic morphology of the colonies such as the shape of a vegetative hypha and the pattern of conidium formation was observed under a microscope. As a result, there was no difference observed except for the color tone. For the color tone, it was found that *Aureobasidium pullulans* M-1 showed a dark green color which is typical for *Aureobasidium pullulans* at the time of the colony observation or the microscopic observation while *Aureobasidium pullulans* M-2 did not show such pigment accumulation properties.

Thus, as shown by the above-mentioned observation, no microbiological properties different from those of the parent strain were observed except for the pigment accumulation properties.

Further, to identify the species, *Aureobasidium pullulans* M-1 and *Aureobasidium pullulans* M-2 were subjected to gene sequence analysis. Specifically, a DNA region containing a ribosomal RNA gene region (1): ITS-5.8S region and a ribosomal RNA gene region (2): 28SrRNA-D1/D2 region, which were located in proximity to each other on a genomic DNA of the *Aureobasidium*, was subjected to PCR amplification using as a primer set a primer ITS5 and a primer NL4 whose base sequences are represented by SEQ ID NO: 1 and 8, respectively, in Sequence Table. Then, a DNA fragment of the amplified product was used as a template to determine the base sequence by thermal cycle sequencing. Table 1 shows a DNA primer used for the DNA amplification and a DNA primer used for the thermal cycle sequencing.

TABLE 1

| Primer | Direction | Base sequence |
|---|---|---|
| rDNA amplification primer | | |
| ITS5 | Forward | SEQ ID NO: 1 |
| NL4 | Reverse | SEQ ID NO: 8 |
| Sequence primer | | |
| ITS5 | Forward | SEQ ID NO: 1 |
| ITS2 | Reverse | SEQ ID NO: 2 |

TABLE 1-continued

| Primer | Direction | Base sequence |
|---|---|---|
| ITS3 | Forward | SEQ ID NO: 3 |
| ITS4 | Reverse | SEQ ID NO: 4 |
| NL1 | Forward | SEQ ID NO: 5 |
| NL2 | Reverse | SEQ ID NO: 6 |
| NL3 | Forward | SEQ ID NO: 7 |
| NL4 | Reverse | SEQ ID NO: 8 |

For the thermal cycle sequencing of the ribosomal RNA gene region (1): ITS-5.8S region in the DNA region, the above-mentioned primer ITS5 was used as a sequence primer, or the primers ITS2, ITS3, and ITS4 whose base sequences are represented by SEQ ID NOS: 2, 3, and 4, respectively, in Sequence Table were used as sequence primers, and the base sequence over a total length of 605 bases was determined using "ABI PRISM 3100 DNA Sequencer" (Tradename, manufactured by Applied Byosystems Ltd.). In addition, for the thermal cycle sequencing of the ribosomal RNA gene region (2): 28SrRNA-D1/D2 region in the DNA region, the above-mentioned primer NL4 was used as a sequence primer, or the primers NL1, NL2, and NL3 whose base sequences were represented by SEQ ID NOS: 5, 6, and 7, respectively, in Sequence Table were used as sequence primers, and the base sequence over a total length of 614 bases was determined in the same manner as described above.

As a result, it was confirmed that the ribosomal RNA gene regions (1) and (2) from the genomic DNA of *Aureobasidium pullulans* M-2 had base sequences represented by SEQ ID NOS: 9 and 10, respectively, in Sequence Table, and that the ribosomal RNA gene regions (1) and (2) from the genomic DNA of *Aureobasidium pullulans* M-1 had base sequences represented by SEQ ID NOS: 11 and 12, respectively, in Sequence Table. The ribosomal RNA gene regions (1) and (2) from the genomic DNA of *Aureobasidium pullulans* M-2 and those from the genomic DNA of *Aureobasidium pullulans* M-1 were 100% homologous, respectively.

In addition, molecular phylogenetic trees for the base sequences of the obtained ribosomal RNA gene regions were created by the neighbor-joining method using the top 20 sequences among analogous sequences detected in an international DNA database. FIG. 1 shows a molecular phylogenetic tree created using the base sequence of the ribosomal RNA gene region (1): ITS-5.8S region, and FIG. 2 shows a molecular phylogenetic tree created using the base sequence of the ribosomal RNA gene region (2): 28SrRNA-D1/D2 region.

The results of the gene sequence analysis confirmed that the mutant strain *Aureobasidium pullulans* M-2 which was created by UV light irradiation was a microorganism belonging to an imperfect fungi *Aureobasidium pullulans* that is the same species as the parent strain *Aureobasidium pullulans* M-1.

Example 2

Production of β-Glucan-Containing Composition

*Aureobasidium pullulans* M-2 was inoculated into 2 L of a liquid nutrient medium (pH 5.2 to 5.4) containing 2.0% of sucrose, 0.2% of rice polishings, and 0.1% of sodium ascorbate, and cultured at an environmental temperature of 25° C. under an aeration and stirring condition of 0.5 v/v/m in a 3-L tank until the culture reaches the proliferation stationary phase (for 120 hours from the inoculation). The resultant cultured product showed a pale milk-white color, so the cultured product lacked the dark green color tone that *Aureobasidium pullulans* generally has.

In addition, to determine a β-glucan content in the cultured product, 100 g of the cultured product was subjected to centrifugation at 1,000 rpm, and high-molecular weight substances in the resultant supernatant were allowed to precipitate using 70% ethanol and then separated by centrifugation. The 70%-ethanol precipitates were treated with enzymes such as α-amylase, protease, and amyloglucosidase to make the high molecular-weight substances other than β-glucan be low molecules. After that, 4-fold volume of 95% ethanol was added thereto to allow β-glucan to be separated as a precipitate moiety. The resultant 95%-ethanol precipitate moiety was subjected to overnight air-dry and then air-dry at 105° C. for 3 hours, and the weight thereof was determined as a β-glucan content.

The cultured product contained 0.7 g (0.7% by mass) of β-glucan with respect to 100 g of the total weight of the cultured product.

Comparative Example 1

Pigment Accumulation Property

To compare the pigment accumulation properties of *Aureobasidium pullulans* M-2 with that of the parent strain *Aureobasidium pullulans* M-1, both strains were cultured with aeration and stirring under the culture condition as shown in Example 2 until the culture reaches the proliferation stationary phase. During the culture period, a part of the cultured products was collected after 72 hours and 264 hours from the inoculation. The collected cultured products were subjected to qualitative analysis for their color components using "spectral colorimeter JS555" (trade name, manufactured by Color Techno System Corporation). Table 2 shows the analysis results as determination values quantified using CIE (International Commission on Illumination) Lab color coordinate system.

TABLE 2

(Color difference determination)

| | Culture period (hr.) | Lightness L* value: JS555 determination |
|---|---|---|
| M-1 (Before pigment production) | 72 | 24.08 |
| M-1 (Pigment production) | 264 | 3.1 |
| M-2 (Before pigment production) | 72 | 29.25 |
| M-2 (Pigment production) | 264 | 26.35 |

The Lab color coordinate system is one of color models that quantify color information, and a color coordinate system standardized by International Commission on Illumination (CIE). It is known that the color coordinate system is composed of a lightness element (L) that indicates a region from black to white, and two color elements (a) that indicates a region from green to red and (b) that indicates a region from blue to yellow, and that the color coordinate system can define a color coordinate space similar to the visual sense of human.

As shown in Table 2, it was clear that the cultured product of *Aureobasidium pullulans* M-2 which had reached the proliferation stationary phase had a significantly high value of the lightness element (L) that indicates a region from black to white as compared with that of the culture composition of the parent strain which had reached the proliferation stationary phase, and thus had a low accumulation properties of the dark green pigment.

Comparative Example 2

β-Glucan Accumulation Property

To compare the β-glucan accumulation property of *Aureobasidium pullulans* M-2 with that of the parent strain *Aureobasidium pullulans* M-1, both strains were cultured with aeration and stirring under the culture condition as shown in Example 2 until the culture reaches the proliferation stationary phase. During the culture period, the cultured products were collected periodically from 48 hours to 264 hours after the inoculation. The β-glucan contents in 100 g each of the culture compositions were determined by the method shown in Example 2. FIG. 3 shows the results.

As shown in FIG. 3, in the culture of the parent strain *Aureobasidium pullulans* M-1, the β-glucan production property thereof decreased after about 72 hours of the culture time had passed, at which accumulation of a melanin-like pigment (dark green pigment) was visually observed. Meanwhile, in the culture of *Aureobasidium pullulans* M-2, β-glucan production continued until the viscosity of the culture solution increased so that the stirring efficiency significantly decreased, and as a result, a culture solution with a high concentration was able to be obtained. In addition, the accumulation amounts of β-glucan between the two strains differed by 1.5 to 3.0 folds after 96 hours from the inoculation.

Test Example 1

The saccharide contained in the nutrient medium was supposed to serve as a raw material for the β-glucan production, so effects of difference in the saccharide concentration on the glucan production were investigated. For this purpose, *Aureobasidium pullulans* M-2 was subjected to culture by shaking on nutrient media having different sucrose concentrations (sucrose concentration: 1, 2, 3, or 4%) under the culture condition as shown in Example 2 until the culture reaches the proliferation stationary phase. After 192 hours from the inoculation, a part of the culture solutions was collected, and the β-glucan contents in 100 g each of the cultured products were determined by the same method as shown in Comparative Example 2. As a result, as shown in FIG. 4, *Aureobasidium pullulans* M-2 produced abundant amounts of β-glucan in every sucrose concentration in the nutrient media, and the accumulation amount thereof was particularly high in the nutrient media containing 2 to 4% of sucrose.

Test Example 2

In general, by maintaining a pH environment in a food processing step acidic, quality deterioration due to saprophytic contamination is difficult to occur, and mild conditions can be adopted when a sterilization treatment is performed as required. Therefore, to investigate the culture conditions regarding the pH environment for *Aureobasidium pullulans* M-2, *Aureobasidium pullulans* M-2 was cultured by shaking using media having different initial pH value at inoculation under the culture condition as shown in Example 2 until the culture reaches the proliferation stationary phase, and a part of the culture solutions was collected after 240 hours from the inoculation. The β-glucan contents in 100 g each of the cultured products were determined by the same method as shown in Comparative Example 2, and the pH value and viscosity of the culture solutions after the culture were determined. Table 3 shows the results. In addition, FIG.

5 shows the results of periodical states of pH value of the culture solutions during the culture of *Aureobasidium pullulans* M-2.

TABLE 3

| Aureobasidium strain | Initial pH | pH after completion of culture | Viscosity (m · Pas) | Content of polysaccharide g/100 g |
|---|---|---|---|---|
| M-2 | 4.5 | 4.4 | 49.4 | 0.744 |
| M-2 | 5.5 | 4.1 | 39.3 | 1.418 |
| M-2 | 7.0 | 4.1 | 49.8 | 1.356 |
| M-2 | 8.0 | 3.9 | 45.2 | 1.342 |
| M-2 | 8.5 | 3.9 | 56.4 | 0.634 |
| M-1 (Parent strain) | 5.5 | 3.8 | 8.7 | 0.405 |

In the visual observation, the cultured products having different initial pH value each had a pale milk-white color tone, so there was no significant difference in the color tone. It was observed that the β-glucan accumulation amount decreased in the culture where the initial pH value at inoculation was 4.5 or 8.5. However, even in those cases, the β-glucan accumulation amounts indicated relatively higher concentrations as compared with that of the parent strain *Aureobasidium pullulans* M-1. In addition, the viscosity of the resultant culture solutions was not pH-dependent, but the viscosity significantly increased as compared with that of the parent strain. Meanwhile, as shown in FIG. 5, the pH value of the culture solutions after culture for a long period of time was apt to converge to pH 3.9 to 4.4. Thus, it was confirmed that, by setting the initial pH value at inoculation of a culture solution to a range from 4.5 to 6.0, *Aureobasidium pullulans* M-2 was able to be cultured in a pH environment in a range of pH 4.5 to 6.0 without any artificial control.

From those results, it was confirmed that *Aureobasidium pullulans* M-2 was able to be suitably cultured under a pH environment in a range from pH 4.5 to 6.0 without receiving effects on the pigment accumulation property and β-glucan accumulation property thereof.

Example 3

High-Functional Yogurt Starter Blended with β-Glucan-Containing Composition

The cultured product (1,000 g) of *Aureobasidium pullulans* M-2 obtained in Example 2 was sterilized under pressure at 121° C. for 15 minutes. After that, 300 g of the cultured product was subjected to a high-speed spinning (1,500 rpm for 20 minutes) using a mixer to make the viscosity thereof low. As a powderization base, 280 g of dextrin (trade name "Sandec" manufactured by Sanwa Cornstarch Co., Ltd.) and/or powdered skimmed milk was added to the cultured product, and the whole was mixed uniformly with a mixer. The resultant product was mixed with the remaining cultured product (700 g), and the whole was freeze-dried and powdered, to thereby obtain a β-glucan-containing composition.

The β-glucan-containing composition was added with 155 g of dextrin (trade name "Sandec" manufactured by Sanwa Cornstarch Co., Ltd.) and/or powdered skimmed milk, 25 g of yogurt powder (including yogurt starter), and 20 g of powdered skimmed milk or the like, to thereby prepare a yogurt starter.

The yogurt starter was a milk-white yogurt starter which showed viscosity and functionality derived from β-glucan in the *Aureobasidium pullulans* culture solution.

Example 4

Skin Moisturizer Blended with β-Glucan-Containing Composition

The cultured product of *Aureobasidium pullulans* M-2 obtained in Example 2 was subjected to centrifugation to obtain a solution without microbial cells, and the solution was sterilized under pressure at 121° for 15 minutes. Then, 30 parts by weight of the solution were added with 2 parts by weight of sorbitol, 2 parts by weight of 1.3-butylene glycol, 1 part by weight of polyethylene glycol, 2 parts by weight of polyoxyethyleine ether, 0.1 part by weight of polyoxyethylene, 10 parts by weight of ethanol, and 52.8 parts by weight of purified water, and appropriate amounts of a pH adjuster, a perfume, an antiseptic, and antioxidant were added thereto to make 100 parts by weight as a whole of a thick emollient.

The resultant emollient was a pale yellow emollient which showed viscosity and functionality derived from β-glucan.

| | "Sequence Table Free Text" |
|---|---|
| SEQ ID NO: 1 | DNA forward primer ITS5 |
| SEQ ID NO: 2 | DNA reverse primer ITS2 |
| SEQ ID NO: 3 | DNA forward primer ITS3 |
| SEQ ID NO: 4 | DNA reverse primer ITS4 |
| SEQ ID NO: 5 | DNA forward primer NL1 |
| SEQ ID NO: 6 | DNA reverse primer NL2 |
| SEQ ID NO: 7 | DNA forward primer NL3 |
| SEQ ID NO: 8 | DNA reverse primer NL4 |
| SEQ ID NO: 9 | Base sequence of a ribosomal RNA gene region (1): ITS-5.8S region which is encoded on a genomic DNA of *Aureobasidium pullulans* M-2 |
| SEQ ID NO: 10 | Base sequence of a ribosomal RNA gene region (2): 28SrRNA-D1/D2 region which is encoded on a genomic DNA of *Aureobasidium pullulans* M-2 |
| SEQ ID NO: 11 | Base sequence of a ribosomal RNA gene region (1): ITS-5.8S region which is encoded on a genomic DNA of *Aureobasidium pullulans* M-1 |
| SEQ ID NO: 12 | Base sequence of a ribosomal RNA gene region (2): 28SrRNA-D1/D2 region which is encoded on a genomic DNA of *Aureobasidium pullulans* M-1 |

Industrial Applicability

The β-glucan-containing composition of the present invention can be utilized for functional foods and drinks, cosmetics, and the like for maintaining or promoting health or beauty.

The invention claimed is:

1. A biologically pure *Aureobasidium pullulans* strain FERM BP-10014.

2. A composition comprising the biologically pure strain of claim 1 that further comprises a liquid medium having a pH value of 4.5 to 6.0.

3. A composition comprising the biologically pure strain of claim 1 and a liquid medium having a pH value of 5.2 to 5.4 containing 1% sucrose, 0.2% ascorbic acid, and 0.2% rice polishings at a temperature of 20° C. to 30° C. under aeration.

4. A method for producing a cultured product containing a β-glucan content of 0.3% or more and/or having a viscosity of 39.3 mPa·s or more comprising:
   culturing the biologically pure strain of claim 1 for a time and under conditions suitable for producing said cultured product; and
   recovering the cultured product.

5. The method of claim 4, further comprising:
   adjusting the pH value of the recovered cultured product to less than 4.5 by addition of vitamin C and/or an organic acid; and
   subjecting the cultured product to heat sterilization.

6. The method of claim 4, wherein said biologically pure strain is cultured in a liquid medium at a pH ranging from 4.5 to 6.0.

7. The method of claim 4, wherein said biologically pure strain is cultured at a temperature ranging from 20 to 30° C. with aeration.

\* \* \* \* \*

SEQUENCE LISTING

<160> NUMBER OF SEQ ID NOS: 12

<210> SEQ ID NO 1
<211> LENGTH: 22
<212> TYPE: DNA

-continued

```
<213> ORGANISM: Artificial sequence
<220> FEATURE:
<223> OTHER INFORMATION: DNA forward primer
<220> FEATURE:
<221> NAME/KEY: misc_feature
<222> LOCATION: (1)..(22)

<400> SEQUENCE: 1
ggaagtaaaa gtcgtaacaa gg                                              22

<210> SEQ ID NO 2
<211> LENGTH: 20
<212> TYPE: DNA
<213> ORGANISM: Artificial sequence
<220> FEATURE:
<223> OTHER INFORMATION: DNA reverse primer
<220> FEATURE:
<221> NAME/KEY: misc_feature
<222> LOCATION: (1)..(20)

<400> SEQUENCE: 2
gctgcgttct tcatcgatgc                                                 20

<210> SEQ ID NO 3
<211> LENGTH: 20
<212> TYPE: DNA
<213> ORGANISM: Artificial sequence
<220> FEATURE:
<223> OTHER INFORMATION: DNA forward primer
<220> FEATURE:
<221> NAME/KEY: misc_feature
<222> LOCATION: (1)..(20)

<400> SEQUENCE: 3
gcatcgatga agaacgcagc                                                 20

<210> SEQ ID NO 4
<211> LENGTH: 20
<212> TYPE: DNA
<213> ORGANISM: Artificial sequence
<220> FEATURE:
<223> OTHER INFORMATION: DNA reverse primer
<220> FEATURE:
<221> NAME/KEY: misc_feature
<222> LOCATION: (1)..(20)

<400> SEQUENCE: 4
tcctccgctt attgatatgc                                                 20

<210> SEQ ID NO 5
<211> LENGTH: 24
<212> TYPE: DNA
<213> ORGANISM: Artificial sequence
<220> FEATURE:
<223> OTHER INFORMATION: DNA forward primer
<220> FEATURE:
<221> NAME/KEY: misc_feature
<222> LOCATION: (1)..(24)

<400> SEQUENCE: 5
gcatatcaat aagcggagga aaag                                            24

<210> SEQ ID NO 6
<211> LENGTH: 26
<212> TYPE: DNA
<213> ORGANISM: Artificial sequence
<220> FEATURE:
<223> OTHER INFORMATION: DNA reverse primer
<220> FEATURE:
<221> NAME/KEY: misc_feature
```

```
<222> LOCATION: (1)..(26)

<400> SEQUENCE: 6
ctctcttttc aaagttcttt tcatct                                              26

<210> SEQ ID NO 7
<211> LENGTH: 26
<212> TYPE: DNA
<213> ORGANISM: Artificial sequence
<220> FEATURE:
<223> OTHER INFORMATION: DNA forward primer
<220> FEATURE:
<221> NAME/KEY: misc_feature
<222> LOCATION: (1)..(26)

<400> SEQUENCE: 7
agatgaaaag aactttgaaa agagag                                              26

<210> SEQ ID NO 8
<211> LENGTH: 19
<212> TYPE: DNA
<213> ORGANISM: Artificial sequence
<220> FEATURE:
<223> OTHER INFORMATION: DNA reverse primer
<220> FEATURE:
<221> NAME/KEY: misc_feature
<222> LOCATION: (1)..(19)

<400> SEQUENCE: 8
ggtccgtgtt tcaagacgg                                                      19

<210> SEQ ID NO 9
<211> LENGTH: 605
<212> TYPE: DNA
<213> ORGANISM: Aureobasidium pullulans
<220> FEATURE:
<221> NAME/KEY: rRNA
<222> LOCATION: (1)..(605)

<400> SEQUENCE: 9
ggaagtaaaa gtcgtaacaa ggtttccgta ggtgaacctg cggaaggatc attaaagagt         60
aagggtgctc agcgcccgac ctccaaccct tgttgttaa aactaccttg ttgctttggc        120
gggaccgctc ggtctcgagc cgctggggat tcgtcccagg cgagcgcccg ccagagttaa        180
accaaactct tgttatttaa ccggtcgtct gagttaaaat tttgaataaa tcaaaacttt        240
caacaacgga tctcttggtt ctcgcatcga tgaagaacgc agcgaaatgc gataagtaat        300
gtgaattgca gaattcagtg aatcatcgaa tctttgaacg cacattgcgc cccttggtat        360
tccgaggggc atgcctgttc gagcgtcatt acaccactca agctatgctt ggtattgggt        420
gccgtcctta gttgggcgcg ccttaaagac ctcggcgagg cctcaccggc tttaggcgta        480
gtagaattta ttcgaacgtc tgtcaaagga gaggacttct gccgactgaa acctttattt        540
ttctaggttg acctcggatc aggtagggat acccgctgaa cttaagcata tcaataagcg        600
gagga                                                                   605

<210> SEQ ID NO 10
<211> LENGTH: 614
<212> TYPE: DNA
<213> ORGANISM: Aureobasidium pullulans
<220> FEATURE:
<221> NAME/KEY: rRNA
<222> LOCATION: (1)..(614)

<400> SEQUENCE: 10
```

-continued

| | | |
|---|---|---|
| gcatatcaat aagcggagga aaagaaacca acagggattg ccctagtaac ggcgagtgaa | 60 | |
| gcggcaacag ctcaaatttg aaagctggcc ttcgggtccg cattgtaatt tgtagaggat | 120 | |
| gctttgggtg aaacgccagt ctaagttcct tggaacagga cgtcatagag ggtgagaatc | 180 | |
| ccgtatgtga ctggaaatgt taacctatgt aaagctcctt cgacgagtcg agttgtttgg | 240 | |
| gaatgcagct ctaaatggga ggtaaatttc ttctaaagct aaatattggc gagagaccga | 300 | |
| tagcgcacaa gtagagtgat cgaaagatga aaagcacttt ggaaagagag ttaaaaagca | 360 | |
| cgtgaaattg ttgaaaggga agcgcttgca atcagacttg tttaaactgt tcggccggtc | 420 | |
| ttctgaccgg tttactcagt ttggacaggc cagcatcagt ttcggcggcc ggataaaggc | 480 | |
| tctgggaatg tggccttcac ttcggtgaag gtgttatagc ccagggtgta atacggccag | 540 | |
| ccgggactga ggtccgcgct tcggctagga tgctggcgta atggttgtaa gcgacccgtc | 600 | |
| ttgaaacacg gacc | 614 | |

<210> SEQ ID NO 11
<211> LENGTH: 605
<212> TYPE: DNA
<213> ORGANISM: Aureobasidium pullulans
<220> FEATURE:
<221> NAME/KEY: rRNA
<222> LOCATION: (1)..(605)

<400> SEQUENCE: 11

| | | |
|---|---|---|
| ggaagtaaaa gtcgtaacaa ggtttccgta ggtgaacctg cggaaggatc attaaagagt | 60 | |
| aagggtgctc agcgcccgac ctccaaccct ttgttgttaa aactaccttg ttgctttggc | 120 | |
| gggaccgctc ggtctcgagc cgctggggat tcgtcccagg cgagcgcccg ccagagttaa | 180 | |
| accaaactct tgttatttaa ccggtcgtct gagttaaaat tttgaataaa tcaaaacttt | 240 | |
| caacaacgga tctcttggtt ctcgcatcga tgaagaacgc agcgaaatgc gataagtaat | 300 | |
| gtgaattgca gaattcagtg aatcatcgaa tctttgaacg cacattgcgc ccttggtat | 360 | |
| tccgaggggc atgcctgttc gagcgtcatt acaccactca agctatgctt ggtattgggt | 420 | |
| gccgtcctta gttgggcgcg ccttaaagac ctcggcgagg cctcaccggc tttaggcgta | 480 | |
| gtagaattta ttcgaacgtc tgtcaaagga gaggacttct gccgactgaa accttttattt | 540 | |
| ttctaggttg acctcggatc aggtagggat acccgctgaa cttaagcata tcaataagcg | 600 | |
| gagga | 605 | |

<210> SEQ ID NO 12
<211> LENGTH: 614
<212> TYPE: DNA
<213> ORGANISM: Aureobasidium pullulans
<220> FEATURE:
<221> NAME/KEY: rRNA
<222> LOCATION: (1)..(614)

<400> SEQUENCE: 12

| | | |
|---|---|---|
| gcatatcaat aagcggagga aaagaaacca acagggattg ccctagtaac ggcgagtgaa | 60 | |
| gcggcaacag ctcaaatttg aaagctggcc ttcgggtccg cattgtaatt tgtagaggat | 120 | |
| gctttgggtg aaacgccagt ctaagttcct tggaacagga cgtcatagag ggtgagaatc | 180 | |
| ccgtatgtga ctggaaatgt taacctatgt aaagctcctt cgacgagtcg agttgtttgg | 240 | |
| gaatgcagct ctaaatggga ggtaaatttc ttctaaagct aaatattggc gagagaccga | 300 | |
| tagcgcacaa gtagagtgat cgaaagatga aaagcacttt ggaaagagag ttaaaaagca | 360 | |
| cgtgaaattg ttgaaaggga agcgcttgca atcagacttg tttaaactgt tcggccggtc | 420 | |

-continued

```
ttctgaccgg tttactcagt ttggacaggc cagcatcagt ttcggcggcc ggataaaggc    480
tctgggaatg tggccttcac ttcggtgaag gtgttatagc ccagggtgta atacggccag    540
ccgggactga ggtccgcgct tcggctagga tgctggcgta atggttgtaa gcgacccgtc    600
ttgaaacacg gacc                                                     614
```